United States Patent [19]

Querry et al.

[11] 4,221,906

[45] Sep. 9, 1980

[54] STABILIZATION OF PNEUMOCOCCAL POLYSACCHARIDES

[75] Inventors: Merle V. Querry, River Vale, N.J.; Francis R. Cano, Spring Valley, N.Y.

[73] Assignee: American Cyanamid Company, Stamford, Conn.

[21] Appl. No.: 21,861

[22] Filed: Mar. 19, 1979

[51] Int. Cl.³ .......................... C07H 1/06; C08B 37/00
[52] U.S. Cl. ........................................ 536/1; 424/180; 424/181
[58] Field of Search ............................................ 536/1

[56] References Cited

U.S. PATENT DOCUMENTS

| | | | |
|---|---|---|---|
| 3,436,311 | 4/1969 | Ferguson et al. | 536/1 |
| 4,043,952 | 8/1977 | Ganslaw et al. | 536/1 |
| 4,090,919 | 5/1978 | Chibala et al. | 536/1 |

OTHER PUBLICATIONS

Dutton et al. "Chem. Abst." vol. 76, 1972 p. 127,306d.
Choy et al. "Can. Jour. of Chem." vol. 51, 1973, pp. 198–207.

*Primary Examiner*—Johnnie R. Brown
*Attorney, Agent, or Firm*—Thomas M. Saunders

[57] ABSTRACT

A method for stabilizing pneumococcal capsular polysaccharide employing glycine or alanine and other amino acids, or albumin, gelatin, protein hydrolysates, and other proteins.

66 Claims, 4 Drawing Figures

STABILIZATION OF PNEUMOCOCCAL POLYSACCHARIDES

BACKGROUND OF THE INVENTION

A multi-valent pneumococcal polysaccharide vaccine, is composed of many types of *Streptococcus pneumoniae* capsular polysaccharide. Normally, these polysaccharides are produced in conventional fermentation. The pneumococcal polysaccharides are separated from other fermentation products by art-recognized methods such as lysing, centrifugation, alcohol fractionation, and ammonium sulfate precipitation. These steps are followed by lyophilization and other purification steps unique to each pneumococcal type. As immunogenicity of the pneumococcal polysaccharides appears to be directly proportional to molecular weight of the polysaccharide (i.e. higher molecular weight equals higher immunogenicity), it is desirable that the pneumococcal capsular polysaccharides be maintained as the largest possible polymers with such polymers retaining the native state structure. This will result in a more effective immunogenic response for a vaccinated subject.

The Bureau of Biologics of the Food and Drug Administration has established standards for the apparent size of all types of pneumococcal polysaccharide polymers used in vaccines. In accordance with their standards, all polysaccharides in present vaccines must have a Kd. value on a Sepharose ® 4B column of less than a range 0.15 to 0.35 (depending on the type of polysaccharide) where Kd. is defined as the $$\frac{V(\text{elution}) - V(\text{void})}{V(\text{bed}) - V(\text{void})}.$$

With Type-19 pneumococcus, the Kd. limit is 0.25 which corresponds to molecular weight of approximately 500,000.

Many of the pneumococcal capsular polysaccharides are sufficiently stable such that the integrity of the molecules are maintained throughout the process of purification of the polysaccharides. Type-19 is exceptional in displaying instability during lyophilization. The Type-19 molecule composed of L-rhamnose, D-glucose, 2-acetamido-2-deoxy-D-mannose and phosphate tends to depolymerize producing molecules with molecular weights below acceptable Kd standards. There is some suggestion that the presence of the phosphate moiety contributes to this observed instability of the polysaccharide.

DESCRIPTION OF THE INVENTION

It has now been discovered that the addition of an amphoteric substance such as glycine, alanine, lysine, valine and other amino acids; albumin, gelatin, peptone, casein and protein hydrolysates and other proteins to a Type-19 capsular pneumococcal polysaccharide before the lyophilization step, at concentrations of 0.01 to 25.0% (V/V) or at a preferred conentration of 0.1 to 0.2% (V/V) stabilizes the polysaccharides so that prohibitive destruction does not occur during lyophilization and, thus, the Bureau of Biologics established standard may be met. Furthermore, the aforementioned additives enhance the solubility of the polysaccharides by lending itself to homogenization thus providing a more useful lyophilized product for later vaccine use.

The mechanism of the protection of the polysaccharide is unclear, however: if the polysaccharide is being enzymatically degraded by residual autolytic enzymes, it is possible that the ionic interaction of the amphoteric substance stereochemically prevents the enzyme from attaching to the active site. For example, the positive charge of the amphoteric substance may be attracted to the phosphorus involved in a phosphodiester bond of the polysaccharide. The presence of the amphoteric substance may prevent the phosphodiesterase from acting at the active site.

If the molecule were degraded because it contained labile bonds that cleaved under the stress of lyophilization (with water molecules being removed), it is possible that the amphoteric substance, by interacting with the labile bond, makes it more resistant to the action of lyophilization.

It is an object of the present invention to effect the preservation of the native state configuration of pneumococcal Type-19 capsular polysaccharides during the steps required to purify the pneumococcal Type-19 capsular polysaccharides from containing sustances.

It is the particular object of this invention to preserve the native state configuration of the capsular polysaccharides in the purification steps wherein the capsular polysaccharides is derived from pneumococcus Type-19.

It is a further object of this invention to stabilize pneumococcal Type-19 capsular polysaccharides during the processes of lyophilization.

Other mechanisms of protective action are also possible, besides those above suggested.

In one embodiment the dried pneumococcal capsular polysaccharide-glycine powder is dissolved in 0.2 M ammonium acetate to a concentration of polysaccharide of 2.5 mg/ml. One milliliter is charged on the column and the Kd determined as mentioned previously. A Kd of less than 0.25 indicates that the molecule has not depolymerized and the polysaccharide is acceptable for use in a vaccine according to the Bureau of Biologics Standards.

Figure 1:
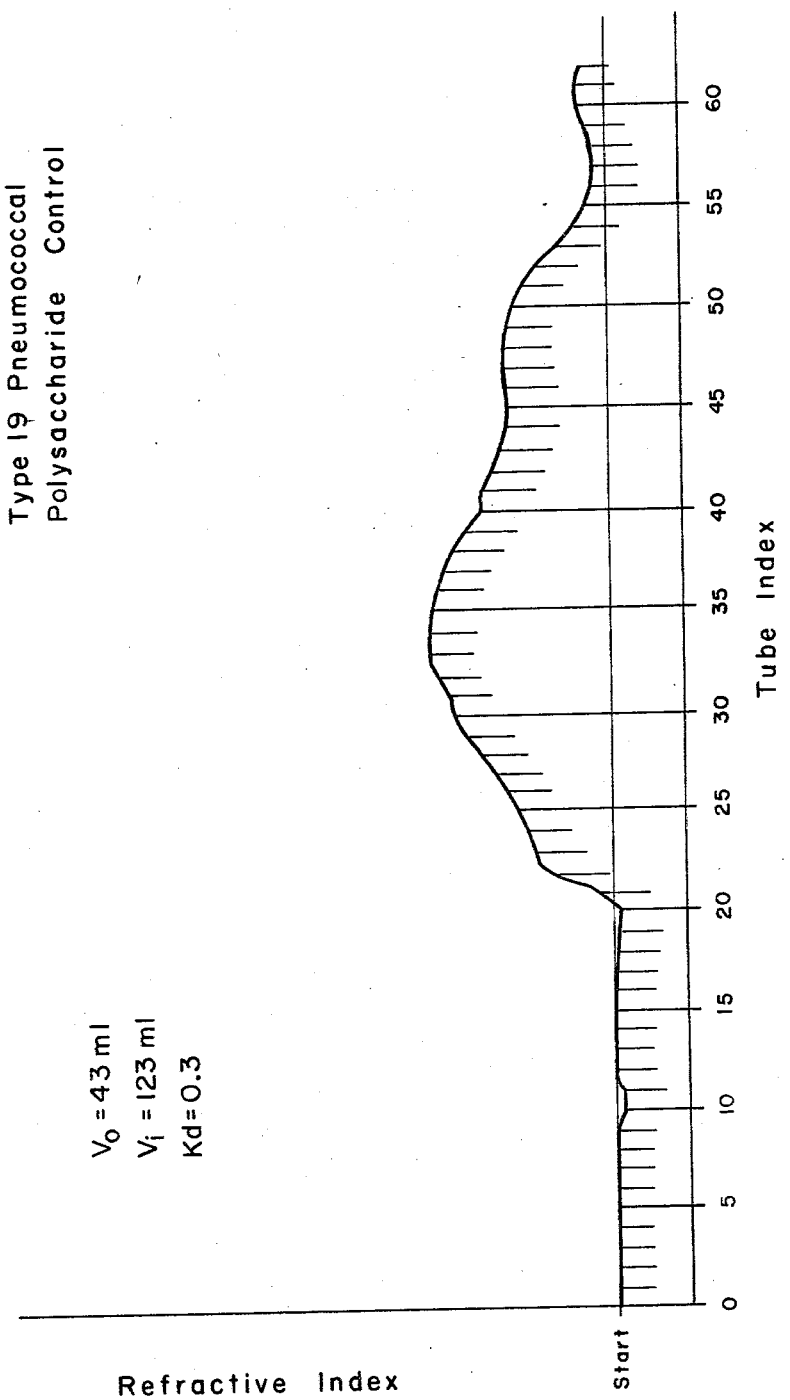
FIG. 1 shows the elution curve of Type-19 polysaccharide without amphoteric stabilizers.
Figure 2:
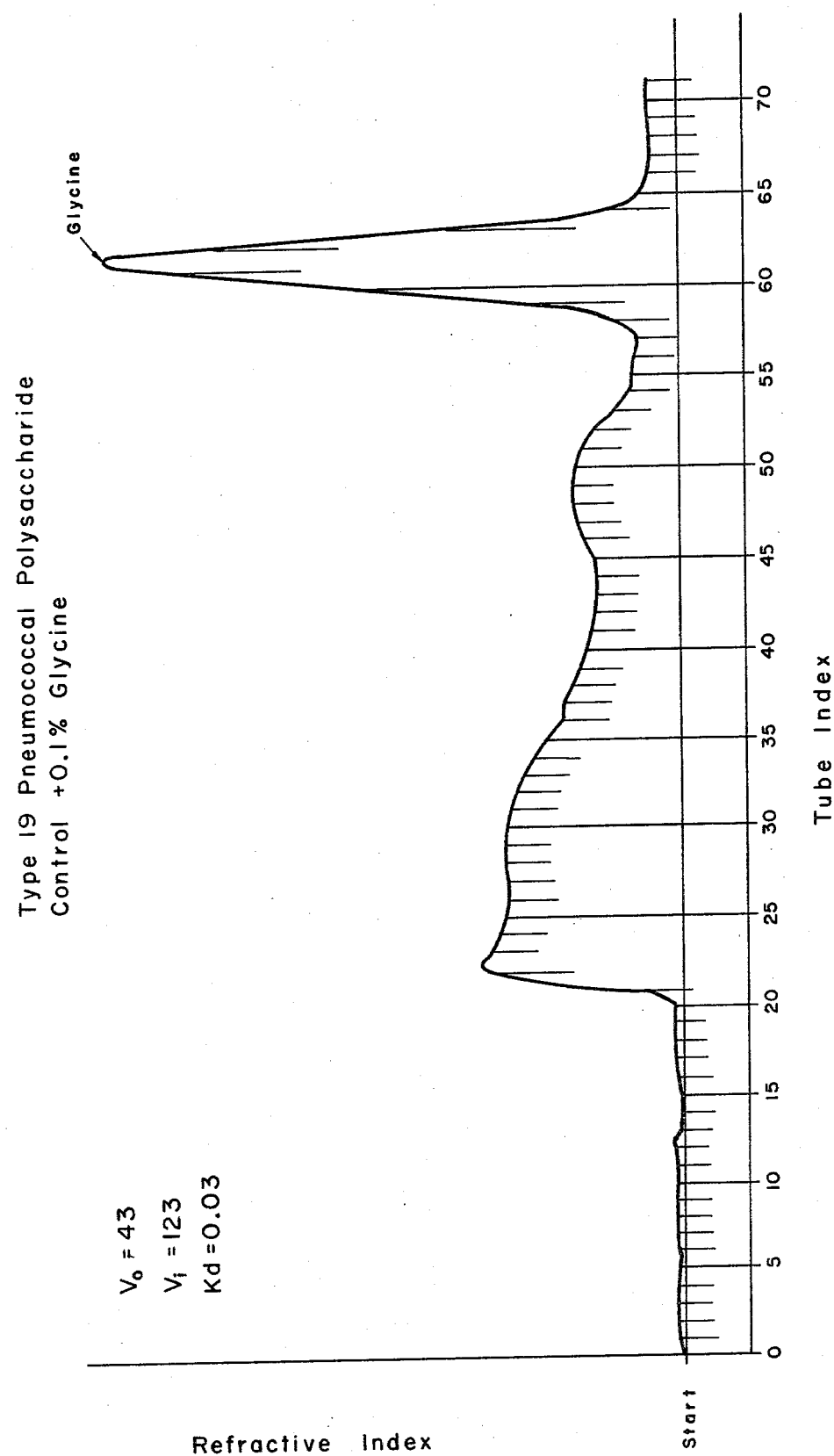
FIG. 2 shows the elution of pneumococcus Type-19 polysaccharide with glycine stabilizers.
Figure 3:
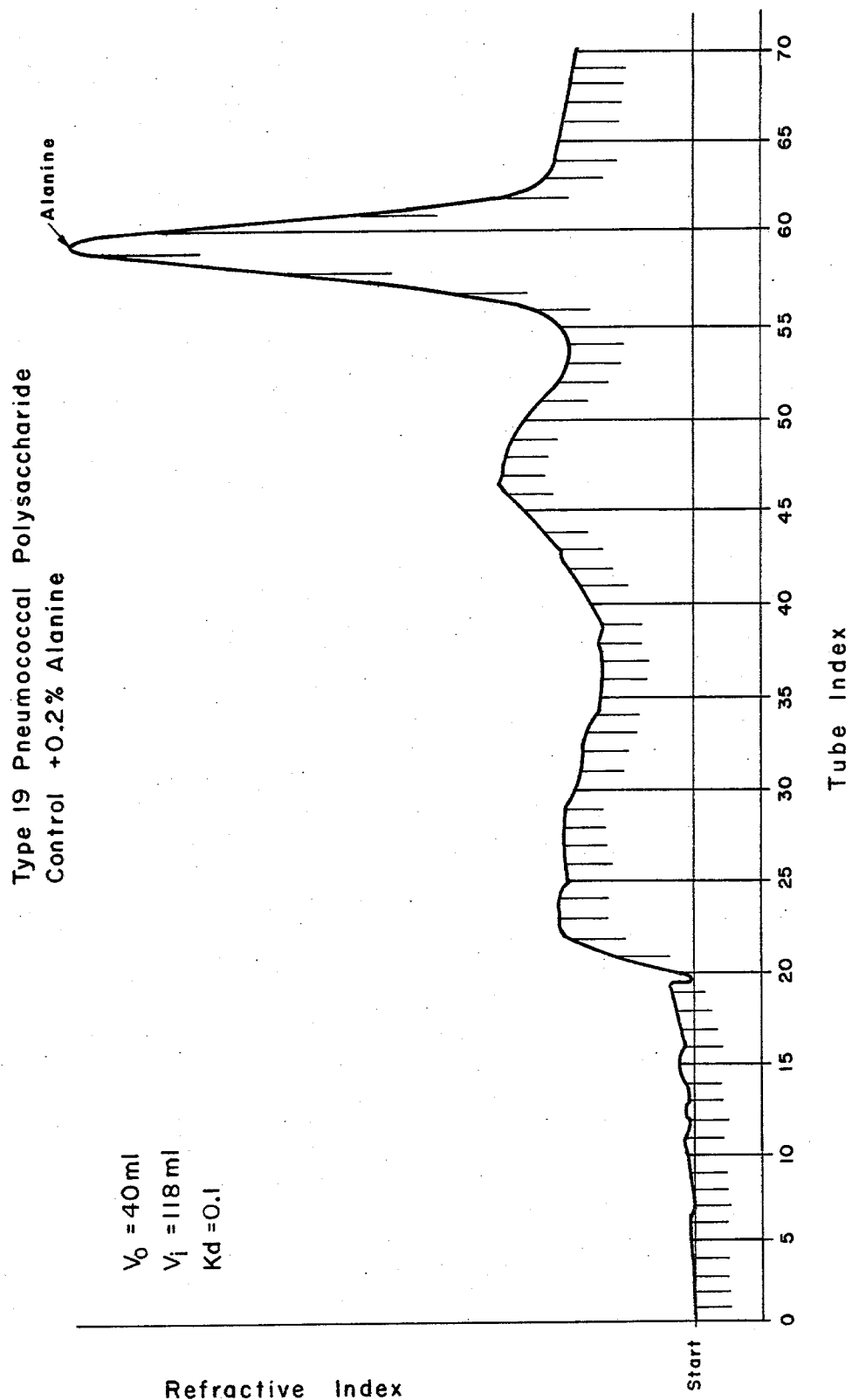
FIG. 3 shows the elution curve of pneumococcus Type-19 polysaccharide with alanine stabilizers.
Figure 4:
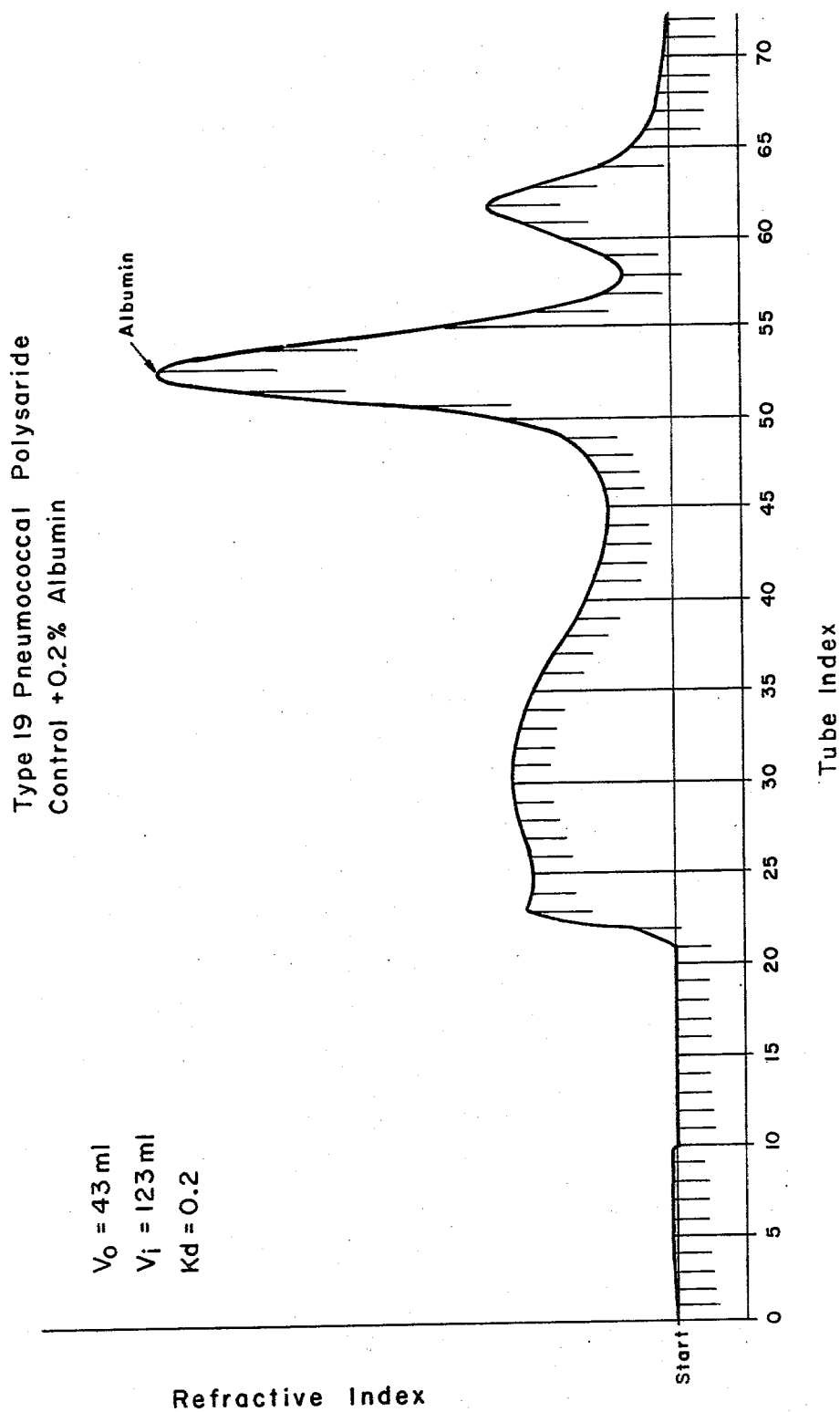
FIG. 4 shows elution curve of the Type-19 polysaccharide with albumin stabilizers.

The importance of this invention, which resides in the stabilization pneumococcal Type-19 polysaccharide molecule by admixture with, for example, glycine, is demonstrated by the attached graphs. FIG. 1 shows an elution curve of an unacceptable lot of unprotected polysaccharide having a Kd of 0.30. FIG. 2 shows an elution curve of an acceptable lot of pneumococcal Type-19 polysaccharide treated with 0.1% glycine having an acceptable Kd of 0.03. FIG. 3 shows an elution curve of an acceptable lot of pneumococcal Type-19 polysaccharide treated with 0.2% DL alanine and having a Kd of 0.1. FIG. 4 shows an elution curve of an acceptable lot of Type-19 polysaccharide treated with 0.2% human serum alubumin and having a Kd of 0.2. Although not graphically presented, other amino acids and proteins would have a similar affect on protecting the polysaccharide from degradation.

The mechanism of protection has not been determined. The two most plausible explanations of the protection from the depolymerization or breakdown of the pneumococcal Type-19 polysaccharide are that it is being enzymatically degraded; or labile bonds such as phosphodiester bonds are being broken or hydrolyzed during lyophilization. However, it is now known that amphoteric substances can protect pneumococcal Type-19 polysaccharide. Also, the protective action appears independent of the size of the stabilizer, be it glycine or albumin. Further ionic interaction appears necessary as neutral compounds such as monosaccharides, disaccharides and polysaccharides do not exert a protective effect.

The invention will first be described in its broadest aspects and then in its more specific application. In accordance with the present invention Sepharose ® 4B [Pharmacia, Piscataway, N.J.] a brand of agarose with an effective molecular separatory range of $3 \times 10^5 - 3 \times 10^6$ $M.W.$ is washed by repeated treatment with 0.2 M ammonium acetate, degassed and packed in a chromatographic column in accordance with manufacturer's specification and by methods well known to the art. The void volume, $V_O$, and the bed volume $V_i$ are determined by dissolving 2.5 mg. of Blue Dextran and 1.0 mg. of glucose in 1.0 ml. of 0.2 M ammonium acetate and applying to the column. 2.0 ml. volumes are collected per tube on a Gilson fraction collector equipped with an eluent marker. The column effluent is monitored by a refractive index [Pharmacia Refractive Index Monitor] and recorded automatically. The first peak at its maximum represents Blue Dextran and the void volume ($V_o$), and the second peak at its maximum represents the bed volume ($V_i$). The elution volume ($V_e$) is determined by dissolving 2.5 mg. of pneumococcal polysaccharide in 1.0 ml. of 0.2 M ammonium acetate and applying it to the column.

The volume of effluent collected to the apex of the first peak represents $V_e$. By substituting the formula $$Kd = \frac{V_e - V_o}{V_i - V_o}$$

the partition coefficient is determined.

When Type-19 pneumococcal capsular polysaccharides are separated in the practice of this invention prior to lyophilization of Type-19 capsular pneumococcal polysaccharides, the amphoteric substances (such as glycine) are added to a concentration of 0.01% to 25% (V/V) are preferably 0.1 to 0.2% (V/V).

The dried pneumococcal capsular polysaccharides and protective substance powder is dissolved in 0.2 M ammonium acetate to a concentration of polysaccharide of 2.5 mg./ml. One milliliter is charged on the column and the Kd. determined as mentioned previously. A Kd. of less than 0.25 indicates that the molecule has not depolymerized below about 500,000 M.W. and polysaccharide of such Kd. value is acceptable for use in vaccine according to the Bureau of Biologic Standards.

The invention will be better understood with reference to the following examples which are illustrative of the invention and not intended as limitations. The invention will be limited specifically in the claims. The invention may be embodied in other forms without departing from the spirit of the invention, and those skilled in the art will immediately be able to recognize many such embodiments.

EXAMPLE 1

In accordance with the present invention Sepharose ® 4B gel (Pharmacia) is suspended in 0.2 M ammonium acetate by careful stirring in order to prevent rupture of the beads. After the gel settles, the fines are decanted and this procedure is repeated until all fines are eliminated. The settled gel is diluted with about three volumes of buffer and transferred to a suction flask. Vacuum is applied and the flask is shaken intermittently for one-half hour to degas the gel suspension. This suspension is carefully poured into a 1.5 × 90 cm Pharmacia column to prevent air bubbles. The bottom outlet of the column is closed until about one-half inch of the gel settles by gravity and then the outlet is opened. The column is packed to a height of about 87 cm. After packing, the column outlet is connected to a Pharmacia Refractive Index monitor and the refractive index (RI) is recorded automatically. The effluent then travels to the Gilson fraction collector where 2.0 ml of effluent is collected per tube. The void volume $V_o$ and the bed volume $V_i$ are determined by dissolving 2.5 mg of Blue Dextran (Pharmacia) and 1.0 mg of dextrose in 1.0 ml of 0.2 M ammonium acetate. One ml. is charged on the column. The mixture flows through the column and the effluent is monitored by refractive index and recorded automatically. The first peak at its maximum represents Blue Dextran and the void volume ($V_o$), and the second peak dextrose at its maximum represents the bed volume ($V_i$). Another method for determining the total bed volume ($V_i$) is with 14C sodium acetate. The column is loaded with 1.0 ml of sodium acetate solution containing $0.4\mu$ Ci radioactivity. Two ml fractions are collected and a 0.5 ml portion for each fraction is transferred into separate scintillation vials containing 10 ml of scintillation liquid. The vials are counted for radioactivity which is expressed as counts per minute. The counts are plotted against the respective fraction numbers. The total bed volume is the volume of eluent collected up to the position of the maximum of the 14C sodium acetate peak in the elution diagram. Symmetrical peaks in the elution profiles are indicative of the acceptability of the column. A 20 ml portion of polysaccharide is lyophilized by standard procedures. The dry polysaccharide is reconstituted at a concentration of 2.5 mg/ml in 0.2 M ammonium acetate and 1.0 ml charged on a previously calibrated Pharmacia column (1.5 × 90 cm) packed with 4B Sepharose ®. At a flow rate of 12-15 ml/hr and a Pharmacia RI monitor range setting suitable to produce a desired height of the elution profile, the polysaccharide flows down the packed Sepharose ® 4B column with the RI automatically recorded. The eluent is collected at 2.0 ml/tube on a Gilson fraction collector. The $V_o$, $V_i$, $V_e$, and Kd. is 43 ml, 123 ml, 67 ml, and 0.3 respectively. FIG. 1 shows that the polysaccharide has been partially degraded with a Kd. of 0.3 which does not meet the requirements of the Bureau of Biologics specifications of 0.25 for Type 19 polysaccharide.

The elution volume ($V_e$) is determined by dissolving 2.5 mg of pneumococcal polysaccharide in 1.0 ml of 0.2 M ammonium acetate and applying it to the column. The volume of effluent collected up to the apex of the first maximum peak represents $V_e$. By substituting in the formula $$KD. = \frac{V_e - V_o}{V_i - V_o},$$

the partition coefficient is determined.

The Kd. of 0.3 when unprotected is contrasted with the protected pneumococcal polysaccharide wherein previous to lyophilization, glycine at a 0.1% concentration is added to 20.0 ml sample. The mixture is lyophilized and the powder dissolved in 0.2 M ammonium acetate to a concentration of 2.5 mg/ml of polysaccharide. One ml is charged on a previously calibrated Pharmacia column (1.5×90 cm) packed with 4B Sepharose. At a flow rate of 12-15 ml/hr and a Pharmacia RI monitor-range setting, suitable to produce a desired height of the elution profile, the polysaccharide flows down the packed column with the RI automatically recorded. The eluent is collected at 2.0 ml/tube on a Gilson fraction collector. The $V_o$, $V_i$, $V_e$, and Kd. is 43 ml, 123 ml, 45 ml, and 0.03, respectively. FIG. 2 shows that glycine has exerted a profound protective effect on the polysaccharide in that it prevented degradation.

EXAMPLE 2

The Type-19 polysaccharide is purified as outlined above. Previous to lyophilization, DL alanine at a concentration of 0.2% is added to a 20 ml sample. The mixture is lyophilized and the powder dissolved in 0.2 M ammonium acetate to a concentration of 2.5 mg/ml of polysaccharide. One ml is charged on a previously calibrated Pharmacia column (1.5×90 cm) packed with Sepharose ® 4B. At a flow rate of 12-15 ml/hr and a Pharmacia RI monitor-range setting suitable to produce a desired height of the elution profile, the polysaccharide flows down the packed column with the RI automatically recorded. The eluent is collected at 2.0 ml/tube on a Gilson fraction collector. The $V_o$, $V_i$, $V_e$, and Kd. is 40 ml, 118 ml, 43 ml, and 0.1 respectively. FIG. 3 shows that DL alanine has exerted a protective effect on the polysaccharide in that it prevented degradation.

EXAMPLE 3

The Type-19 polysaccharide is purified as outlined in Example 1 above. Previous to lyophilization, normal human serum albumin is added at a concentration of 0.2% to a 20 ml sample of polysaccharide. The mixture is lyophilized and the powder dissolved in 0.2 M ammonium acetate to a concentration of 2.5 mg/ml of polysaccharide. One ml is charged on a previously calibrated Pharmacia column (1.5×90 cm) packed with Sepharose ® 4B. At a flow rate of 12-15 ml/hr and a Pharmacia RI monitor-range setting suitable to produce the desired height of the elution profile, the polysaccharide flows down the packed column with the RI automatically recorded. The eluent is collected at 2.0 ml/tube on a Gilson fraction collector. The $V_o$, $V_i$, $V_e$, and Kd. is 43 ml, 123 ml, 59 ml and 0.2, respectively. FIG. 4 shows that normal human serum albumin has exerted a protective effect on the polysaccharide in that it prevented degradation.

The above examples are illustrative of the invention and in no way to be considered limiting. It will be clear to those skilled in the art that any amphoteric substance of the broad classification will serve to protect the molecular integrity of the capsular polysaccharide. It may be found, for example, that polysaccharides that have hitherto been found labile in the lyophilization step will be protected by the addition of amphoteric substances. In particular, those skilled in the art will also be able to recognize that other amino acids will protect capsular polysaccharides in the lyophilization step without departing from the spirit of the invention. Other proteins and protein hydrolysates will be found to protect the capsular polysaccharide in the lyophilization step without departing from the spirit of the invention. It will further be obvious to those skilled in the art that capsular polysaccharides from several types and from several organisms will be protected in other lyophilization purification procedures by amino acids and proteins and protein hydrolysates without departing from the spirit of the invention.

What is claimed is:

1. In a process of purifying Type-19 pneumococcal capsular polysaccharide wherein pneumococcal capsular polysaccharides are produced in fermentation and partially isolated therefrom and lyophilized wherein the improvement comprises stabilizing the Type-19 pneumococcal capsular polysacharides during lyophilization by adding an effective stabilizing amount of glycine to the prelyophilate mixture.

2. The process of claim 1 wherein the improvement comprises stabilizing the Type-19 pneumococcal capsular polysaccharide during lyophilization by adding glycine to the prelyophilate mixture in concentrations of 0.01 to 25% V/V.

3. The process of claim 1 wherein the improvement comprises stabilizing the Type-19 pneumococcal capsular polysaccharide during lyophilization by adding glycine to the prelyophilate mixture in concentrations of 0.1 to 2% V/V.

4. In a process of purifying Type-19 pneumococcal capsular polysaccharide wherein pneumococcal capsular polysaccharides are produced in fermentation and partially isolated therefrom and lyophilized wherein the improvement comprises stabilizing the Type-19 pneumococcal capsular polysaccharides during lyophilization by adding an effective stabilizing amount of alanine to the prelyophilate mixture.

5. The process of claim 4 wherein the improvement comprises stabilizing the Type-19 pneumococcal capsular polysaccharide during lyophilization by adding alanine to the prelyophilate mixture in concentrations of 0.01 to 25% V/V.

6. The process of claim 4 wherein the improvement comprises stabilizing the Type-19 pneumococcal capsular polysaccharide during lyophilization by adding alanine to the prelyophilate mixture in concentrations of 0.1 to 2% V/V.

7. In a process of purifying Type-19 pneumococcal capsular polysaccharide wherein pneumococcal capsular polysaccharides are produced in fermentation and partially isolated therefrom and lyophilized wherein the improvement comprises stabilizing the Type-19 pneumococcal capsular polysaccharides during lyophilization by adding an effective stabilizing amount of albumin to the prelyophilate mixture.

8. The process of claim 7 wherein the improvement comprises stabilizing the Type-19 pneumococcal capsular polysaccharide during lyophilization by adding albumin to the prelyophilate mixture in concentrations of 0.01 to 25% V/V.

9. The process of claim 7 wherein the improvement comprises stabilizing the Type-19 pneumococcal capsular polysaccharide during lyophilization by adding albumin to the prelyophilate mixture in concentration of 0.2 to 0.4% V/V.

10. In a process of purifying Type 19 pneumococcal capsular polysaccharide wherein capsular polysaccharides are produced in fermentation and partially isolated therefrom and lyophilized wherein the improvement comprises stabilizing said polysaccharides during lyophilization by adding an effective stabilizing amount of amphoteric substance.

11. The process of claim 10 comprising stabilizing said polysaccharide during lyophilization by adding said amphoteric substance to the prelyophilate mixture in concentrations of 0.01 to 25% V/V.

12. The process of claim 11 comprising stabilizing said polysaccharide during lyophilization by adding amphoteric substance to the prelyophilate mixture in concentrations of 0.1 to 2% V/V.

13. The process of claim 10, or 11, or 12 wherein the amphoteric substance is an amino acid.

14. The process of claim 13 wherein the amino acid is selected from the group consisting of lysine, alanine, valine, glycine and combinations thereof.

15. The process of claim 14 wherein the amino acid is valine.

16. The process of claim 14 wherein the amino acid is lysine.

17. The process of claim 10, or 11 or 12 wherein the amphoteric substance is a protein.

18. The process of claim 17 wherein the protein is selected from the group consisting of albumin, casein, gelatin and combinations thereof.

19. The process of claim 18 wherein the protein is gelatin.

20. The process of claim 18 wherein the protein is casein.

21. The process of claim 10, or 11, or 12 wherein the amphoteric substance is a protein hydrolysate.

22. The process of claim 21 wherein the protein hydrolysate is a hydrolysate selected from the group consisting of albumin, casein, peptone, gelatin and combinations thereof.

23. The process of claim 22 wherein the hydrolysate in a hydrolysate of albumin.

24. The process of claim 22 wherein the hydrolysate is a hydrolysate of casein.

25. The process of claim 22 wherein the hydrolysate is a hydrolysate of gelatin.

26. The process of claim 22 wherein the hydrolysate is a peptone.

27. In a process of purifying capsular polysaccharide wherein capsular polysaccharides are produced in fermentation and partially isolated therefrom and lyophilized wherein the improvement comprises stabilizing the capsular polysaccharides during lyophilization by adding an effective stabilizing amount of amphoteric substance.

28. The process of claim 27 comprising stabilizing the capsular polysaccharide during lyophilization by adding said amphoteric substance to the prelyophilate mixture in concentrations of 0.01 to 25% V/V.

29. The process of claim 28 comprising stabilizing the capsular polysaccharide during lyophilization by adding amphoteric substance to the prelyophilate mixture in concentrations of 0.1 to 2% V/V.

30. The process of claim 27, or 28, or 29 wherein the amphoteric substance is an amino acid.

31. The process of claim 30 wherein the amino acid is selected from the group consisting of lysine, alanine, valine, glycine and combinations thereof.

32. The process of claim 31 wherein the amino acid is valine.

33. The process of claim 31 wherein the amino acid is lysine.

34. The process of claim 31 wherein the amino acid is glycine.

35. The process of claim 31 wherein the amino acid is alanine.

36. The process of claim 27, or 28 or 29 wherein the amphoteric substance is a protein.

37. The process of claim 36 wherein the protein is selected from the group consisting of albumin, casein, gelatin and combinations thereof.

38. The process of claim 37 wherein the protein is gelatin.

39. The process of claim 37 wherein the protein is albumin.

40. The process of claim 37 wherein the protein is casein.

41. The process of claim 27, or 28, or 29 wherein the amphoteric substance is a protein hydrolysate.

42. The process of claim 41 wherein the protein hydrolysate is a hydrolysate selected from the group consisting of albumin, casein, peptone, gelatin and combinations thereof.

43. The process of claim 42 wherein the hydrolysate is a hydrolysate of albumin.

44. The process of claim 42 wherein the hydrolysate is a hydrolysate of casein.

45. The process of claim 42 wherein the hydrolysate is a hydrolysate of gelatin.

46. The process of claim 42 wherein the hydrolysate is a peptone.

47. In a process of purifying pneumococcal capsular polysaccharide wherein pneumococcal capsular polysaccharides are produced in fermentation and partially isolated therefrom and lyophilized wherein the improvement comprises stabilizing the pneumococcal capsular polysaccharides during lyophilization by adding an effective stabilizing amount of amphoteric substance.

48. The process of claim 47 comprising stabilizing the pneumococcal capsular polysaccharide during lyophilization by adding said amphoteric substance to the prelyophilate mixture in concentrations of 0.01 to 25% V/V.

49. The process of claim 48 comprising stabilizing the pneumococcal capsular polysaccharide during lyophilization by adding said amphoteric substance to the prelyophilate mixture in concentrations of 0.1 to 2% V/V.

50. The process of claim 47, or 48, or 49 wherein the amphoteric substance is an amino acid.

51. The process of claim 50 wherein the amino acid is selected from the group consisting of lysine, alanine, valine, glycine and combinations thereof.

52. The process of claim 51 wherein the amino acid is valine.

53. The process of claim 51 wherein the amino acid is lysine.

54. The process of claim 51 wherein the amino acid is glycine.

55. The process of claim 51 wherein the amino acid is alanine.

56. The process of claim 47, or 48, or 49 wherein the amphoteric substance is a protein.

57. The process of claim 56 wherein the protein is selected from the group consisting of albumin, casein, gelatin and combinations thereof.

58. The process of claim 57 wherein the protein is gelatin.

59. The process of claim 57 wherein the protein is albumin.

60. The process of claim 57 wherein the protein is casein.

61. The process of claim 47, or 48, or 49 wherein the amphoteric substance is a protein hydrolysate.

62. The process of claim 61 wherein the protein hydrolysate is a hydrolysate selected from the group consisting of albumin, casein, peptone, gelatin and combinations thereof.

63. The process of claim 62 wherein the hydrolysate is a hydrolysate of albumin.

64. The process of claim 62 wherein the hydrolysate is a hydrolysate of casein.

65. The process of claim 62 wherein the hydrolysate is a hydrolysate of gelatin.

66. The process of claim 62 wherein the hydrolysate is a peptone.